United States Patent [19]

Stookey

[11] 4,117,109

[45] Sep. 26, 1978

[54] DENTIFRICE PREPARATION

[75] Inventor: George K. Stookey, Noblesville, Ind.

[73] Assignee: Indiana University Foundation, Bloomington, Ind.

[21] Appl. No.: 651,447

[22] Filed: Jan. 22, 1976

[51] Int. Cl.$^2$ .......................... A61K 7/16; A61K 7/18
[52] U.S. Cl. ...................................... 424/57; 424/49; 424/52
[58] Field of Search .................................. 424/49–54, 424/57

[56] References Cited

U.S. PATENT DOCUMENTS

| 3,012,852 | 12/1961 | Nelson | 424/52 |
| 3,804,946 | 4/1974 | Harrison | 424/52 |
| 3,989,814 | 11/1976 | Cordon et al. | 424/57 |

Primary Examiner—Natalie Trousof
Assistant Examiner—Cary Owens
Attorney, Agent, or Firm—Kirkland & Ellis

[57] ABSTRACT

Dentifrice preparations exhibiting optimum cleaning ability and reduced abrasion may be obtained by employing therein low levels of a dental abrasive material (e.g., about 10–20% calcium pyrophosphate) in combination with an inert filler and one or more detergent agents. Additionally, increased therapeutic effectiveness may be achieved where anticariogenic adjuvants such as sodium fluoride, NaF, and stannous fluoride, $SnF_2$, are incorporated in such dentifrice preparations.

4 Claims, No Drawings

DENTIFRICE PREPARATION

BACKGROUND OF THE INVENTION

1. Field of the Invention

The present invention relates to new dentifrice preparations and more particularly to dentifrice preparations comprising low levels (e.g., about 10–20%, by weight) of a dental abrasive material in combination with an inert filler and one or more detergent agents. Such preparations exhibit significantly reduced abrasion levels, yet surprisingly are as effective in cleaning the teeth as conventional dentifrices containing abrasives at the usual levels of about 40% weight. In addition, where therapeutic anticariogenic agents are incorporated in such preparations, enhanced therapeutic effects are achieved as a result of the reduced abrasive levels.

2. Description of the Prior Art

Dental research has developed substantial evidence that beyond the age of forty years loss of teeth is predominantly the result of periodontal involvement rather than dental caries. A factor contributing to periodontal disease is the accumulation of dental plaque and calculus (e.g., salivary tartar) on the teeth. These accumulations result in tissue inflammation of the surrounding gingiva, and, as the condition increases in severity, the supporting bone is also affected. These reactions lead to the destruction of the supporting structures and the subsequent mass loss of teeth.

Heretofore, commercially available dentifrice preparations containing abrasives such as calcium pyrophosphate ($Ca_2P_2O_7$) insoluble sodium metaphosphate ($NaPO_3)x$, and calcium hydrogen phosphate dihydrate/anhydrous calcium hydrogen phosphate ($CaHPO_4 \cdot 2H_2O/CaHPO_4$), have employed relatively high levels of abrasives (e.g., about 40% by weight). While certain of these abrasives, especially calcium pyrophosphate, have demonstrated highly satifactory levels of cleaning and consequently have been effective in preventing the accumulation of materia alba, oral debris, plaque, pellicle, stains, and dental calculus, such preparations have been unduly abrasive and damaging to the oral hard tissues.

Dental researchers have been increasingly concerned about the levels of abrasion experienced with such dentifrice preparations, and it has heretofore been proposed to reduce abrasion levels by lowering the amounts of abrasive employed. In recent years gel-type dentifrices containing as little as 25% abrasive have been commercially used. However, although such products have been somewhat less abrasive, they have also performed much less satisfactorily from a cleaning standpoint.

The beneficial effects, in terms of a reduction in the incidence of dental caries, resulting from the incorporation of water-soluble fluoride salts, such as stannous fluoride, are well known. However, efforts to utilize such anticariogenic agents in dentifrices suitable for home use have been handicapped by the tendency for fluoride ions to be inactivated and rendered unavailable by other ingredients, particularly the abrasive component of such dentifrices. While generally speaking, dentifrice abrasives in therapeutic products used today are to varying degrees compatible with fluoride agents, there is a wide variation in compatibility. Moreover, the high levels of abrasives required to achieve the desired cleaning performance has, in addition to undesirable abrasion, also adversely affected the available anticariogenic agent levels.

Thus, prior art dentifrice preparations have been unsatisfactory in one or more of the following respects, namely, relatively poor cleaning and polishing performances (especially with respect to prevention of reaccumulation of dental calculus, pellicle, materia alba, and the more resistant forms of oral hard tissue stains and pigmentations), incompatibility with fluoride-containing anticariogenic agents, and adverse abrasion.

Accordingly, it is a primary object of the present invention to provide dentifrice preparations which exhibit superior cleaning and reduced abrasion.

Another object of the present invention is to provide dentifrice preparations of the character described which are effective in removing stained dental pellicle and similar exogenous accretions.

Another object of the present invention is to provide dentifrice preparations having enhanced anticariogenic agent availability.

SUMMARY OF THE INVENTION

The foregoing and other objects, advantages, and features of this invention may be achieved with a dentifrice preparation comprising about 10–20%, by weight, of a dental abrasive material; about 8–15% of an inert filler; and from 0.5%–5.0% of one or more detergent agents. The dentifrice preparations of this invention may in addition comprise anticariogenically effective and nontoxic amounts of at least one fluoride-containing anticariogenic agent.

Calcium pyrophosphate $Ca_2P_2O_7$, is the preferred dental abrasive material and low particle size synthetic silica is the preferred filler.

The dentifrice preparations of the present invention permit the desired high level of cleaning to be achieved with dramatically reduced abrasion levels. Surprisingly, these reduced abrasion levels obtained through the use of reduced levels of dental abrasive materials, are achieved without adversely affecting cleaning ability. In addition, where anticariogenic agents are employed in the dentifrice preparations, higher levels of agent availability are experienced due to the lower levels of abrasives employed in the dentifrice.

DESCRIPTION OF THE PREFERRED EMBODIMENTS

In accordance with the present invention, high cleaning, low abrasion dentifrice preparations comprise from about 10 to 20%, by weight, of a dental abrasive material; from about 8–15% of an inert filler; and from about 0.5 to about 5.0% of one or more detergent agents.

Dentifrice preparations in accordance with this invention may also employ anticariogenically effective and nontoxic amounts of fluoride-containing anticariogenic agents such as stannous fluoride, sodium fluoride, or the like.

Primary benefits of this invention have been produced through the use of the predominantly beta phase calcium pyrophosphate described in U.S. Pat. No. 3,112,247, granted Nov. 26, 1963. Such calcium pyrophosphate dental abrasives have been widely used on a commercial basis in dentifrice preparations. Although U.S. Pat. No. 3,112,247 describes dentifrices comprising about 20–40%, preferably about 30–40%, by weight, abrasive, such commercial dentifrices employing these calcium pyrophosphate abrasives have contained about 40% abrasive, by weight, in order to achieve the level of cleaning desired.

In accordance with this invention, it has now been found that only about 10-20%, preferably about 12.5%, of such calcium pyrophosphate may be satisfactorily employed and that higher levels of abrasive are not required to achieve desired levels of cleaning. Moreover, such dentifrices exhibit dramatically reduced abrasion levels in comparison with the prior commercial products.

In combination with such reduced levels of calcium pyrophosphate, inert filler material is employed in order to provide bulk to the preparation and to provide consumer-acceptable bulk flow properties. The composition of such filler material is not critical although it should be non-toxic and should be of extremely low particle size in order not to effect adversely the abrasion levels off the overall dentifrice preparation. The filler material should also be compatible with fluoride agents in the event a therapeutic product is desired. Preferred inert fillers, in accordance with this invention, include low particle size synthetic silicas. Suitable materials include fumed silicas having particle sizes ranged from <1 up to about 30 microns commercially available from Davison Chemical Division, W. R. Grace & Co., under the trademarks "Syloid 74" and "Syloid 620", respectively. Talcs and the like are also suitable inert fillers.

Dental preparations in accordance with this invention generally contain from about 8 to about 15% of the inert filler, preferably about 15%, by weight.

Because of the reduced levels of the abrasive constituent of the dentifrice preparations of this invention, the detergent component of the preparation occupies a significant role in maintaining the cleaning performance of the dentifrice preparation. Suitable detergent agents include one or more surface active, wetting and sudsing agents including, but not limited to, water-soluble alkyl sulfates having from 8 to 18 carbon atoms in the alkyl radical, such as sodium lauroyl sulfate, water-soluble salts of sulfonated monoglycerides of fatty acids having from 10 to 18 carbon atoms in the alkyl radical such as sodium coconut monoglyceride sulfonate, salts of fatty acid amides of taurines such as sodium N-methyl palmitoyl taurine, and salts of fatty acid esters of isethionic acid. Such detergent agents may be used in the compositions of this invention in amounts of from about 0.5%, to about 5.0% by weight of the total composition.

Preferred detergent systems in accordance with this invention include sodium N-lauroyl sarcosinate at a level of about 1.5-2.5% by weight; a mixture of about 0.75-1.5% sodium N-lauroyl sarcosinate and about 0.75-1.5% sodium alkyl sulfate; a mixture of about 0.75-1.5% sodium N-lauroyl sarcosinate with about 0.75-1.5% monoglyceride sulfonate; a mixture of about 1.5-2.5% monoglyceride sulfonate and about 0.75% sodium alkyl sulfate; and a mixture of about 1.5-2.5% sodium alkyl sulfate and about 0.75% monoglyceride sulfonate.

The dentifrice preparations of the subject invention are prepared in a conventional manner and usually include additional ingredients which render the over-all composition commercially acceptable to consumers.

Thus, they require a binder substance to impart desired textural properties. Natural gum binders such as gum tragancanth, gum karaya, gum arabic, etc., and seaweed derivative, such as sodium carboxymethyl cellulose can be used for this purpose. Desirably, those materials are employed which are most compatible with fluoride ion. Improvements in texture can also be attained by including an additional material such as colloidal magnesium aluminum silicate. Bindings in an amount of from about 0.5% to about 5.0%, by weight, can be sued to form a satisfactory toothpaste.

It is also desirable to include some humectant material in a toothpaste to keep it from hardening. Materials commonly used for this purpose include glycerine, sorbitol, and other polyhydric alcohols. The humectants can comprise up to 35% of conventional toothpaste compositions.

Finally, flavoring materials may be included in a toothpaste formulation including small amounts of oils or wintergreen and peppermint and sweetening agents such as saccharin, dextrose, and levulose.

Compositions of exemplary non-fluoride dentifrice preparations of the present invention are given in the following Example 5.

EXAMPLE I

| Constituent | Parts by Weight |
| --- | --- |
| Calcium Pyrophosphate | 12.50 |
| Filler (Syloid 74 synthetic silica) | 15.00 |
| Water | 37.00 |
| Glycerin | 10.00 |
| Sorbitol | 20.00 |
| Sodium coconut monoglyceride sulfonate | 1.50 |
| Sodium-N-lauroyl sarcosinate | 1.50 |
| Veegum (Magnesium aluminum silicate) | 0.40 |
| Sodium carboxymethyl cellulose | 0.70 |
| Flavorings, colorings, etc. | 1.00 |

EXAMPLE II

| Constituent | Parts by Weight |
| --- | --- |
| Calcium Pyrosphosphate | 17.50 |
| Filler (Syloid 74 synthetic silica) | 11.00 |
| Water, Deionized | 36.20 |
| Glycerine | 10.00 |
| Sorbitol | 20.00 |
| Carboxymethyl Cellulose | 0.70 |
| Veegum | 0.40 |
| Saccharin | 0.20 |
| Monoglyceride Sulfonate | 1.50 |
| Sodium N-lauroyl Sarcosinate | 1.50 |
| Flavorings, Coloring, etc. | 1.00 |

EXAMPLE III

| Constituent | Parts by Weight |
| --- | --- |
| Calcium Pyrophosphate | 15.00 |
| Filler (Syloid 74 synthetic silica) | 12.00 |
| Water, Deionized | 37.80 |
| Glycerine | 10.00 |
| Sorbitol | 20.00 |
| Carboxymethyl Cellulose | 0.70 |
| Veegum | 0.40 |
| Saccharin | 0.20 |
| Monoglyceride Sulfonate | 2.25 |
| Sodium Alkyl Sulfate | 0.75 |
| Flavorings, Coloring, etc. | 0.90 |

As previously indicated, the dentifrice preparations of the present invention also preferably contain anticariogenically effective and non-toxic amounts of water-soluble fluoride-containing anticariogenic adjuvants in anticariogenic dentifrice preparations. Preferably, the adjuvant is present in the form of water-soluble fluoride-containing compounds capable of supplying fluoride. The preferred adjuvant is sodium fluoride, NaF, although other materials such as stannous fluorizirconate ($SnZrF_6$), indium fluorozirconate ($InZrF_7$), stannous fluoride ($SnF_2$), and complex zirconium-germanium fluorides [e.g., $Zr(GeF_6)_2$, $ZrGeF_8$, $Ge(ZrF_6)_2$, and $Zr(GeF_6]$ may be employed. Sodium fluoride is preferred by reason of anticariogenic effectiveness obtainable therewith.

Other suitable adjuvants include water-soluble fluoride salt such as $SnF_4$, $KF$, $InF_3$, $PbF_2$, $FeF_2$, and $LiF$, as well as more complex water-soluble fluoride-containing adjuvants such as sodium and potassium difluorooxalatostannate (II) complexes of U.S. Pat. No. 3,721,691; fluorosilicates, e.g., $Na_2SiF_6$, other fluorozirconates, e.g., $CaZrF_6$, $Na_2ZrF_6$, fluorostannites, e.g., $NaSnF_3$, fluoroborates, e.g., $NaBF_4$, fluorotitanates, e.g., $NaTiF_5$, other fluorogermanates, e.g., $K_2GeF_6$, and mixed halides, e.g., $SnClF$ and $Sn_2ClF_3$. Mixtures of suitable adjuvants may also be utilized. Another suitable adjuvant comprises a mixture of a fluoride salt and an active phosphate compound such as Victamide as set forth and described in U.S. Pat. No. 3,666,855, issued May 30, 1972.

In general, an anticariogenic dentifrice preparation produced in accordance with the subject invention will contain from about 0.05 up to 1.0%, by weight, of the dentifrice preparation of the fluoride-containing anticariogenic adjuvant so as to desirably provide about 1000 ppm fluoride ion. Sodium fluoride is preferably provided at a level of 0.22%, by weight, and, when $SnF_2$ is utilized, the desired amount is preferably about 0.4%.

Preferably, such fluoride-containing dentifrice preparations are employed in their natural pH ranges (i.e., about 4.5 to 7.5), although, if desired, the pH range may be adjusted to about 4 to 9 with acetic acid, sodium hydroxide or various sodium phosphates, or other buffering agents.

Exemplary formulations of fluoride-containing dentifrices in accordance with this invention are given in the following Examples.

EXAMPLE IV

| Constituent | Parts by Weight |
|---|---|
| Calcium pyrophosphate | 12.50 |
| Filler (Syloid 74 synthetic silica) | 15.00 |
| Water | 37.00 |
| Stannous fluoride | 0.40 |
| Sodium carboxymethyl cellulose | 0.70 |
| Veegum (Magnesium aluminum silicate) | 0.40 |
| Sorbitol | 20.00 |
| Glycerin | 10.00 |
| Sodium N-lauroyl sarcosinate | 1.50 |
| Sodium coconut monoglyceride sulfonate | 1.50 |
| Flavorings, colorings, etc. | 1.00 |

EXAMPLE V

| Constituent | Parts by Weight |
|---|---|
| Calcium Pyrophosphate | 15.00 |
| Filler (Syloid 74 synthetic silica) | 12.00 |
| Water (deionized) | 37.67 |
| Glycerine | 10.00 |
| Sorbitol | 20.00 |
| Sodium Fluoride | 0.22 |
| Monoglyceride sulfonate | 1.50 |
| Sodium alkyl sulfate | 0.75 |
| Veegum | 0.40 |
| Saccharin | 0.20 |
| Carboxymethyl cellulose | 0.70 |
| Sodium Phosphate, Hydrated, Dibasic | 0.28 |
| Sodium Phosphate, Monohydrate, Monobasic | 0.28 |
| Flavoring, Coloring, etc. | 1.00 |

EXPERIMENTAL EVALUATIONS

The superiority of the dentifrice preparations disclosed herein has been substantiated by the following experimental evaluations.

Tooth dentin is frequently found exposed at the surface of the teeth near the free gingival margin particularly in clinical cases where the gingivae have receded. The abrasion of tooth dentin by a dentifrice preparation is much greater than the abrasion of tooth enamel by the same composition, i.e., 10-100 times. Consequently, dentin abrasion is considered to be of greater clinical importance than enamel abrasion, and the effect of a dentifrice preparation on dentin is used as an important and reliable criterion in the selection of suitable compositions. The dentifrice preparations utilized in accordance with the subject invention have highly satisfactory dentin abrasion characteristics.

A method for determining dentin abrasion values for dentifrice preparations is as follows. The dentin portions are separated from human central incisors and exposed to neutron radiation whereby a predetermined portion of phosphate content is converted to $P^{32}$. Each dentin portion is mounted in a selfcuring polymer, such as methyl methacrylate, and is submerged in a slurry of the dentifrice to be tested. An automatic toothbrush is arranged so that it can be moved back and forth across the surface of the submerged portion of the dentin, and the pressure of this toothbrush is adjusted to 150 grams. The tooth dentin is subjected to brushing action for a given number of strokes, and removed from the slurry. The radioactivity of the slurry is then determined by conventional means. An equivalent piece of dentin, irradiated concurrently with the dentin portion to be brushed, is weighed, dissolved in hydrochloric acid, and the radioactivity determined. Using this as a standard, the amount of tooth dentin removed during the brushing can be determined by comparing the count of the brushing slurry with the count of the standard. The standard radioactive solution is also combined with the various slurries and counted to determine the amount of self-absorption attributable to the specific abrasive system being evaluated.

A standard slurry for measuring dentin abrasion is made from calcium pyrophosphate ($Ca_2P_2O_7$). The concentration of the standard slurry is 10.0 grams per 50 cc. of a 0.5 percent aqueous sodium carboxymethyl cellulose −10% glycerine solution.

To determine the abrasion value of a dentifrice preparation, a portion of irradiated tooth dentin is first brushed with a standard calcium pyrophosphate slurry. The same portion of dentin is then cleaned with water and brushed with a slurry of a dentifrice to be tested. The dentin is again cleaned and brushed with the standard calcium pyrophosphate slurry. Each of these slurries is counted, the average amount of radioactive dentin removed by the brushing with the slurries of standard calcium pyrophosphate and with the cleaning and polishing agent being tested are calculated. The amount of dentin removed by the standard calcium pyrophosphate slurry is given an arbitrary value of 500. The factor required to effect the conversion of the amount of dentin removed to this value is 500 is multiplied times the average amount of dentin removed by brushing with the cleaning and polishing agent being tested.

The cleaning ability of a dentifrice preparation may be evaluated in the laboratory as follows. Initially, a readily visibly deposit of stained pellicle is formed on prepared enamel specimens, typically bovine enamel specimens, by suspending them from a rotating (2rpm) rod which rotates intermittently through a trough containing the pellicle-forming media in an incubator at 37° C. The pellicle-forming media consists of trypticase soy broth, gastic mucin, instant tea, instant coffee, and sarcina lutea (chromogenic bacteria). The enamel specimens are subjected to continuous intermittent bathing in the pellicle-forming media for 96 hours with the pellicle-forming media replenished at approximate 10–12 hour intervals. At the conclusion of this period the specimens are coated with a heavy, visible pellicle which is chemically and physically similar to that observed in humans.

The pellicle-coated specimens are then scored with the aid of a binocular microscope and distributed into the desired specimen groups on the basis of the initial or pretest scores. One group of specimens is treated with a standard dentifrice and serves as an internal reference while the remaining groups of specimens are treated with experimental dentifrices. Treatments are administered with a mechanical toothbrushing machine equipped with soft, nylon toothbrushes, a load or tension of 150 grams on the toothbrushes, and a brushing exposure of 800 double strokes. The dentifrices are tested as slurries consisting of 25 g dentifrice and 40 ml. water.

The treated enamel specimens are then scored again, and a comparison of the pre-test and post-test scores used to indicate the amount of pellicle removed by the dentifrices. In order to eliminate bias, the specimens are numerically coded and randomized prior to each scoring. Further, the entire test is normally repeated on a second set of prepared specimens, and the findings of the two tests pooled. The findings are reported in terms of a cleaning ratio expressed on the basis of the internal standard dentifrice in each test with the higher scores indicative of greater cleaning or pellicle removal. The internal reference standard dentifrice, a commercially available dentifrice containing about 40% by weight, calcium pyrophosphate has been routinely assigned an arbitraty value of 130.

Using the foregoing techniques, dentin abrasion values and cleaning ratios were obtained for a variety of commercially available dentifrices. All of the commercial products contained dental abrasive material at a level of about 38–42%, by weight, with the exception of Commercial Dentifrice VI, which contained about 27%, by weight, of a silica abrasive. These data are reported in Table I, which also contains a Cleaning Efficiency Ratio for each. The Cleaning Efficiency Ratio is obtained by dividing the cleaning ratio by the dentin abrasion value.

TABLE I

| Dentifrice Identification | Abrasive Identity | Average Dentin Abrasive Value* (RDA) | Average Cleaning Ratio** (CR) | Cleaning Efficiency (CR/RDA) |
|---|---|---|---|---|
| Commercial I | $Ca_2P_2O_7$ | 660 | 130 | 0.197 |
| Commercial II | $Ca_2P_2O_7$ | 663 | 106.5 | 0.161 |
| Commercial III | $Na(PO_3)_x/CaHPO_4$ | 634 | 118 | 0.186 |
| Commercial IV | $CaHPO_4/CaHPO_4 \cdot 2H_2O$ | 498 | 68.5 | 0.138 |
| Commercial V | $CaHPO_4/CaHPO_4 \cdot 2H_2O$ | 729 | 90.5 | 0.124 |
| Commercial VI | $SiO_2$ | 701 | 84. | 0.120 |
| Commercial VII | $Al_2O_3 \cdot 3H_2O$ | 799 | 83. | 0.104 |
| Commercial VIII | $CaCO_3$ | 1073 | 109. | 0.102 |

*Average values of several replicates performed over a period of 15 months.
**Average of several replicates.

The data of Table I demonstrate generally unsatisfactorily high abrasion levels experienced with commercial dentifrices. The data also show that efforts to reduce abrasion by using less abrasive materials (e.g., Commercial Dentifrice IV) have resulted in poor cleaning performance. Similarly, Commercial Dentifrice VI, which decreased the abrasive content to 27% caused cleaning performance to be reduced with no corresponding reduction in abrasion.

As a result, it was both surprising and unexpected to find that the dentifrice preparation of Example I of this invention; when subjected to laboratory comparison with Commercial Dentifrice I containing nearly three times the amount of the same calcium pyrophosphate abrasive, cleaned at virtually the same level as the commercial product, yet was only about half as abrasive. These data are reported in Table II.

TABLE II

| Dentifrice Identification | Abrasive Identity | Abrasive Amount | Average Dentin Abrasive Value (RDA) | Average Cleaning Ratio* (CR) | Cleaning Efficiency (Cr/RDA) |
|---|---|---|---|---|---|
| Commercial I | $Ca_2P_2O_7$ | 40% | 592 ± 25 | 130 ± 9 | 0.220 |
| Example I | $Ca_2P_2O_7$ | 12.5% | 297 ± 5** | 115 ± 13 | 0.387 |

*The cleaning ratios are not significantly different (p < 0.05)
**Standard error of the mean Human clinical cleaning measurement also demonstrates that the dramatic reductions in abrasion of the dentifrice preparations of this invention are achieved without sacrificing cleaning ability.

Clinical evaluations of dentifrice cleaning may be performed in the following manner. Participants in these studies are adults who have been previously screened and observed to collect stained pellicle when using a standard calcium pyrophosphate dentifrice during a 4–6 week period. The subjects were then stratified according to smoking habit (smoker or non-smoker) and pre-test pellicle score into the desired number of groups. All subjects are then given a thorough prophylaxis to remove all stained pellicle. For convenience, examinations were restricted to the labial surfaces of the 12 anterior teeth. The participants were then given another prophylaxis and a different dentifrice for a second 4-week period. At the conclusion of this period the patients were again examined for stained pellicle. The cross-over process was continued until each participant used each product. All studies were performed in a double-blind manner to eliminate the possibility of bias. A numerical scale was used to quantify the stained pellicle observed, with a higher score indicating heavier accumulations of stained pellicle. The values are presented in terms of the average total score per patient. Thus, lower numerical scores are indicative of lesser amounts of stained pellicle formation and better cleaning ability.

A study was conducted in the foregoing manner with teh Example I dentifrice preparation of this invention and with Commercial Dentifrice I. The results of this cross-over type study are reported in Table III.

TABLE III

| Dentifrice | Mean Pellicle Score* |
|---|---|
| Example I | 4.03 |
| Commercial I | 3.82 |

*These values are not significantly different at $\alpha = 0.05\%$ as determined by analysis of variance.

The compatibility of dentifrice preparations as carrier vehicles for fluoride-containing adjuvants may be determined by obtaining the amount of available fluoride ion in solution. Percentage availability refers to a comparison fo an ionic concentration level for a reference solution of the adjuvant without the carrier vehicle (e.g., an aqueous solution of the adjuvant maintained at a reference ionic concentration level, such as 1,000 ppm fluoride). A percentage ratio of the ionic concentration level for the combination solution relative to the reference solution is determined by conventional techniques. Thus, a combination solution of carrier vehicle and sodium fluoride which analyzes 900 ppm fluoride concentration compared to a reference solution of sodium fluoride at 1,000 ppm fluoride exhibits a 90% availability insofar as ability to provide fluoride ions is concerned.

Table IV reports percentage availability data for the Example I dentifrice and, for comparison, for Commercial Dentifrice I as well. These data demonstrate the greater fluoride compatability of the preparations of this invention.

TABLE IV

| Dentifrice | Per Cent Availability (F) After 3 Months Storage At Indicated Temperatures | |
|---|---|---|
| | 75° F | 100° F |
| Example I | 99.7 | 74.7 |
| Commercial I | 85.1 | 66.1 |

Finally, enamel polishing studies have shown that the dentifrices of this invention are not significantly different from a polishing standpoint than commercial product containing the same abrasive at a 40% level.

The lingual surfaces of freshly extracted maxillary anterior teeth were reduced with the aid of a water-colored carborundum wheel and the teeth were reduced mounted by means of methyl methacrylate resin on rectangular jigs constructed so as to fit the movable stage of a reflectometer. The exposed labial surface of each tooth was mounted in such a manner that the height of the contour was a suitable distance above the base of the jig. Throughout the procedure, care was taken to insure that the teeth did not become dry to prevent damage to tooth tissues. The exposed enamel surface was then dulled by exposing it to 0.10% hydrochloric acid (pH2.2) for 30 seconds. Any acid remaining on the tooth surface was neutralized by immediately transferring the tooth to a saturated sodium carbonate solution for 30 seconds. The tooth was then rinsed with water and blotted dry.

The maximum reflectance of the dulled tooth surface was determined by means of a reflectometer especially adapted to detect the changes in the degree of polish of the enamel surface. The reflectometer is constructed so that the enamel is exposed to a beam of polarized light, the amount of light reflected from the enamel surface was determined by a photoelectric cell which in turn activated a galvanometer. The smoother the enamel surface, the smaller the amount of diffused and absorbed light and, hence, the higher the galvanometer reading.

After the maximum reflectance of the dulled tooth was determined, the tooth was brushed with the dentifrice to be tested. After the tooth was treated, the enamel surface was rinsed with water so as to remove any residual particles of the cleaning and polishing agent, and the reflectance of the enamel surface was again measured with the tooth located in exactly the same position as that used to obtain the "dull" reading. The absolute change in the amount of reflectance between the dull and polished enamel surfaces was taken as a measure of the degree of polishing imparted by the treatment.

The foregoing enamel polish procedure was utilized for Commercial Dentifrice I and the Example I Dentifrice with the reflectometer measurements periodically being made throughout a total brushing period of 30,000 strokes. The results are expressed in Table V in terms of the mean increment in the luster of the enamel specimens.

TABLE V

| Brushing Period (Number Strokes) | Mean Increment in Enamel Polish | |
|---|---|---|
| | Commercial I | Example I |
| 5,000 | 4.28 ± 0.39 | 4.74 ± 0.31 |
| 10,000 | 5.50 ± 0.31 | 5.79 ± 0.25 |
| 20,000 | 6.31 ± 0.31 | 6.60 ± 0.24 |
| 30,000 | 6.75 ± 0.28 | 7.06 ± 0.26 |

The differences in the enamel polish profiles of the two dentifrices are not statistically significant in spite of the substantial difference in the amount of calcium pyrophosphate present in the formulations.

The foregoing data are supportive of the significant and surprising dental health advance that may be achieved by utilizing dentifrice preparations of this invention.

I claim:

1. A paste type dentifrice preparation comprising:
   from about 10 up to about 20%, by weight calcium pyrophosphate;
   from about 8 up to about 15%, by weight, of an inert filler comprising low particle size silica; and
   from about 0.5 to about 5.0% of at least one detergent.

2. A dentifrice preparation, as claimed in claim 1, wherein the detergent agent is a member selected from the group consisting of sodium coconut monoglyceride sulfonate, sodium N-lauroyl sarcosinate, sodium alkyl sulfate, and mixtures thereof.

3. A dentifrice preparation, as claimed in claim 1, and further comprising an anticariogenically effective and nontoxic amount of at least one fluoride-containing anticariogenic adjuvant.

4. A dentifrice preparation, as claimed in claim 3, wherein the anticariogenic adjuvant is sodium fluoride.

* * * * *